United States Patent [19]
Frank et al.

[11] Patent Number: 5,824,271
[45] Date of Patent: Oct. 20, 1998

[54] GAS SENSOR

[75] Inventors: Joachim Frank, Ottobrunn; Maximilian Fleischer, Höhenkirchen; Hans Meixner, Haar, all of Germany

[73] Assignee: Siemens Aktiengesellschaft, Munich, Germany

[21] Appl. No.: 809,264

[22] PCT Filed: Sep. 11, 1995

[86] PCT No.: PCT/DE95/01242

§ 371 Date: Mar. 13, 1997

§ 102(e) Date: Mar. 13, 1997

[87] PCT Pub. No.: WO96/08712

PCT Pub. Date: Mar. 21, 1996

[30] Foreign Application Priority Data

Sep. 14, 1994 [DE] Germany .......................... 44 32 729.3

[51] Int. Cl.⁶ .............................................. G01N 27/403
[52] U.S. Cl. ........................ 422/98; 422/94; 422/95; 422/96; 422/97; 436/134; 436/137; 436/141; 436/149; 436/153; 73/23.2; 73/23.31; 73/31.06; 338/34
[58] Field of Search ................. 422/94, 95, 96, 422/97, 98; 436/149, 153, 132, 134, 141; 73/23.31, 31.06, 23.2; 338/34

[56] References Cited

U.S. PATENT DOCUMENTS

| | | | |
|---|---|---|---|
| 4,001,756 | 1/1977 | Heijne | 338/34 |
| 4,033,169 | 7/1977 | Fujishiro et al. | 73/23 |
| 4,322,968 | 4/1982 | Takomi et al. | 73/27 R |
| 4,387,359 | 6/1983 | Tien et al. | 338/34 |
| 4,481,499 | 11/1984 | Avina et al. | 73/31.06 |
| 5,298,783 | 3/1994 | Wu | 257/414 |
| 5,431,883 | 7/1995 | Barraud | 422/98 |
| 5,602,324 | 2/1997 | Yanagida et al. | 73/23.2 |
| 5,618,496 | 4/1997 | Hasumi et al. | 73/31.06 |

FOREIGN PATENT DOCUMENTS

| | | |
|---|---|---|
| 0 056 752 A1 | 11/1982 | European Pat. Off. |
| 0 464 243 A1 | 4/1990 | European Pat. Off. |
| 0 464 244 A1 | 4/1990 | European Pat. Off. |
| 0 527 259 A1 | 3/1991 | European Pat. Off. |
| 0 563 613 A2 | 4/1993 | European Pat. Off. |
| 05 4210 397 A1 | 3/1992 | Germany . |
| 05 4210 398 A1 | 3/1992 | Germany . |
| 42 03 522 C1 | 7/1992 | Germany . |
| 6222026 | 12/1994 | Japan . |

Primary Examiner—Jill Warden
Assistant Examiner—Sharidan Carrillo
Attorney, Agent, or Firm—Hill & Simpson

[57] ABSTRACT

A substrate carrying a first electrode and a second electrode, the first and second electrodes being disposed adjacent to one another, the first electrode being disposed between the substrate and a gas-sensitive component, the gas sensitive component comprising an n-type semiconductor, the gas-sensitive component having a resistance that is gas-dependent and temperature-dependent, and the second electrode being disposed between the substrate and a non-gas-sensitive component, the non-gas-sensitive component comprising a n-type semiconductor and a p-type semiconductor, the non-gas-sensitive component having a resistance that is temperature-dependent and that is not gas-dependent and wherein the n-type semiconductor of the non-gas-sensitive component is $Ga_2O_3$ and the p-type semiconductor of the non-gas-sensitive component is $ZrO_2$.

10 Claims, 5 Drawing Sheets

GAS SENSOR

FIELDS OF THE INVENTION

The invention relates to a gas sensor based on gallium oxide, for the detection of oxidizing or reducing gases.

BACKGROUND OF THE INVENTION

Gallium oxide sensors are known and are disclosed in EP 0 464 243 "oxygen sensor with semiconducting gallium oxide" and EP 0 464 244 "sensor for the detection of reducing gases". The electrical resistance, and also the gas sensitivity, of $Ga_2O_3$ are strongly temperature-dependent. In order to obtain a gas-sensitive effect, $Ga_2O_3$ gas sensors must be operated in a gas-specific temperature range. Currently available $Ga_2O_3$ gas sensors need to be thermally regulated very accurately to within this range, so that a temperature fluctuation does not induce the same resistance change as would have been caused by a change in the concentration of the gas to be detected. In order to ensure a sufficiently constant operating temperature, a highly elaborate hardware outlay is necessary. The sensitivity of the overall system is strongly limited by the remaining system deviation. In the case of strong and frequent temperature fluctuations, signal evaluation is only conditionally possible, since the control system reacts only after a delay.

If a part of the sensor arrangement is covered with a gas-impermeable layer, in order to use this part, which is thereby passivated, for temperature compensation, as is disclosed in the refinements of EP 0 464 243 or EP 0 464 244, the following problem arises. The originally gas-impermeable layer, which is applied to a gas-sensitive part in order to cover it, becomes cracked and therefore gas-permeable over time. That part of the sensor arrangement which is intended only to be temperature-dependent also becomes gas-sensitive as a result of the gas which penetrates the cover layer through the cracks, which greatly vitiates the measurement.

A further possibility of using a part of the sensor arrangement for temperature compensation consists in doping it with metal atoms, for example gold, so heavily that it loses its gas sensitivity. This is described in DE 42 10 397 or DE 42 10 398. A disadvantage with this is that the doped part of the sensor arrangement is not stable.

SUMMARY OF THE INVENTION

The object of the invention is to provide a gas sensor which provides two output signals, one of them having gas dependence and temperature dependence, and the other merely having the temperature dependence.

A suitable combination of the two output signals advantageously provides a compensated signal which is independent of temperature fluctuations.

The present invention provides a gas sensor that comprises a substrate that carries a first electrode and a second electrode. The electrodes are preferably disposed on the substrate adjacent to one another. The first electrode is further disposed between the substrate and a gas-sensitive component, in the form of an arrangement, housing or structure. The gas-sensitive component comprises an end-type semiconductor and further has a resistance that is gas-dependent as well as temperature-dependent.

The second electrode of the present invention is disposed between the substrate and a non-gas-sensitive component, also in the form of an arrangement, housing or structure. The non-gas-sensitive component comprises an n-type semiconductor and a p-type semiconductor and further has a resistance that is temperature-dependent but that is not gas-dependent.

In an embodiment, the n-type semiconductor of the gas-sensitive component is $Ga_2O_3$.

In an embodiment, the n-type semiconductor of the non-gas-sensitive component is $Ga_2O_3$.

In an embodiment, the n-type semiconductor of the non-gas-sensitive component is $Ga_2O_3$ and the p-type semiconductor of the non-gas-sensitive component is $ZrO_2$.

In an embodiment, the n-semiconductor of the non-gas-sensitive component is at least one layer of n-type semiconductor material and the p-semiconductor of the non-gas-sensitive component is at least one layer of p-type semiconductor material. In a preferred embodiment, the ratio of the thicknesses of the p-semiconductor material layer to the overall thickness of the non-gas-sensitive component ranges from about 0.05 to about 0.2. In a preferred embodiment, the layers of the non-gas-sensitive component are heat treated at temperatures ranging from about 900° C. to about 1050° C.

In a preferred embodiment, the electrodes are interdigital components.

An advantage of the present invention is that it provides a gas sensor that is capable of detecting reducing gasses at temperatures ranging from about 600° C. to about 850° C.

Yet another advantage of the present invention is that it provides a gas sensor that is capable of detecting oxygen at a temperature range of about 950° C.

BRIEF DESCRIPTION OF THE DRAWINGS

The invention will be explained in more detail below with the reference to the figures.

It should be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular embodiments illustrated herein.

Figure 1:
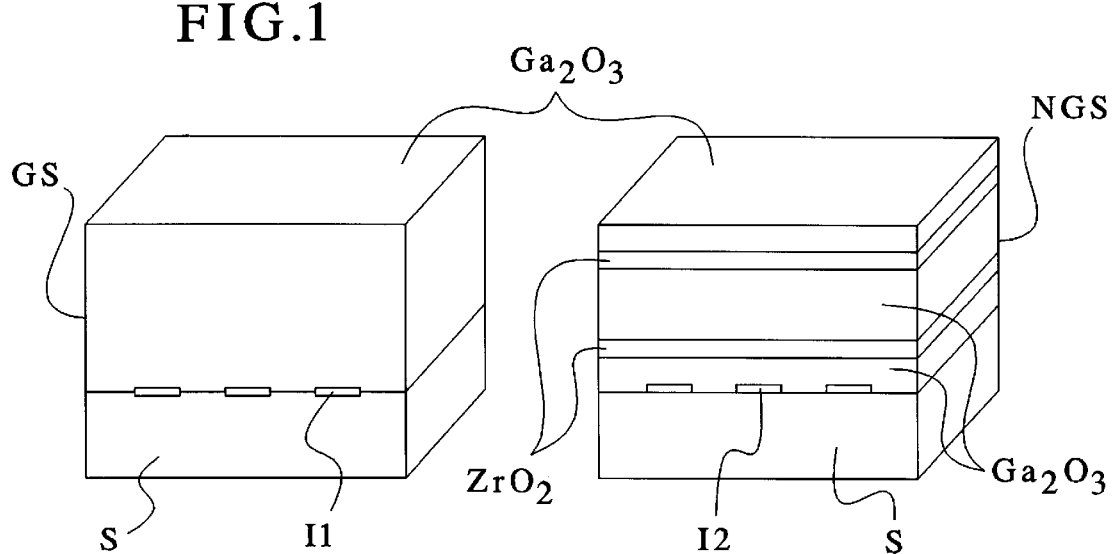
FIG. 1 illustrates, schematically, a gas-sensitive component and a non-gas-sensitive component of a gas sensor made in accordance with the present invention.

By using the reference resistor shown on the right-hand side in FIG. 1, the non-gas-sensitive part NGS of the gas sensor, and the electrical resistance of the gas-sensitive sensor part GS (cf. FIG. 1, left) the ratio or the difference between the two resistances can be compared in order to produce a signal which is only dependent on the type of gas and no longer on temperature fluctuations. Both NGS and GS of the gas sensor have the same temperature dependence of electrical resistance.

The gas-sensitive arrangement (cf. FIG. 1, left) is produced by reactive sputtering, the basis for the gas-sensitive material being an n-type semiconductor, for example $Ga_2O_3$ ceramic. To this end, about 25% of oxygen is added to the sputtering gas argon. The non-gas-sensitive arrangement NGS is produced likewise, with the difference that, in this arrangement, one or more intermediate layers of a p-type semiconductor, for example $ZrO_2$, are applied as non-gas-sensitive material. For this purpose, the $Ga_2O_3$ sputtering process is interrupted. The material of the intermediate layer $ZrO_2$ is sputtered, likewise reactively, with the addition of oxygen. This is followed by another $Ga_2O_3$ layer, and so on. The total layer thicknesses for $Ga_2O_3$ and $ZrO_2$ should be selected in such a way that about 5 to 20% of the total layer thickness of the arrangement consists of $ZrO_2$.

By variations in the layer thicknesses, the resistances may, if appropriate, be matched to one another.

The total layer thickness of the respective arrangement is between 1–10 $\mu$m, 1–4 layers being typically used.

$ZrO_2$ is a gas-permeable material. The gas permeability is, however, not a decisive criterion for the operability of the sensor. Instead, it must be ensured that layers of p-type and n-type semiconductors are located in the non-gas-sensitive part NGS of the sensor.

The production process takes place as follows. Firstly, the non-gas-sensitive arrangement NGS is produced on the substrate S, with the region where the gas-sensitive arrangement GS is later to be produced being covered. After this, the gas-sensitive arrangement GS is produced, with the region in which the non-gas-sensitive gas sensor part NGS has already been produced being covered. This sequence ensures that the $ZrO_2$ in no case contaminates the gas-sensitive arrangement GS.

Figure 2:
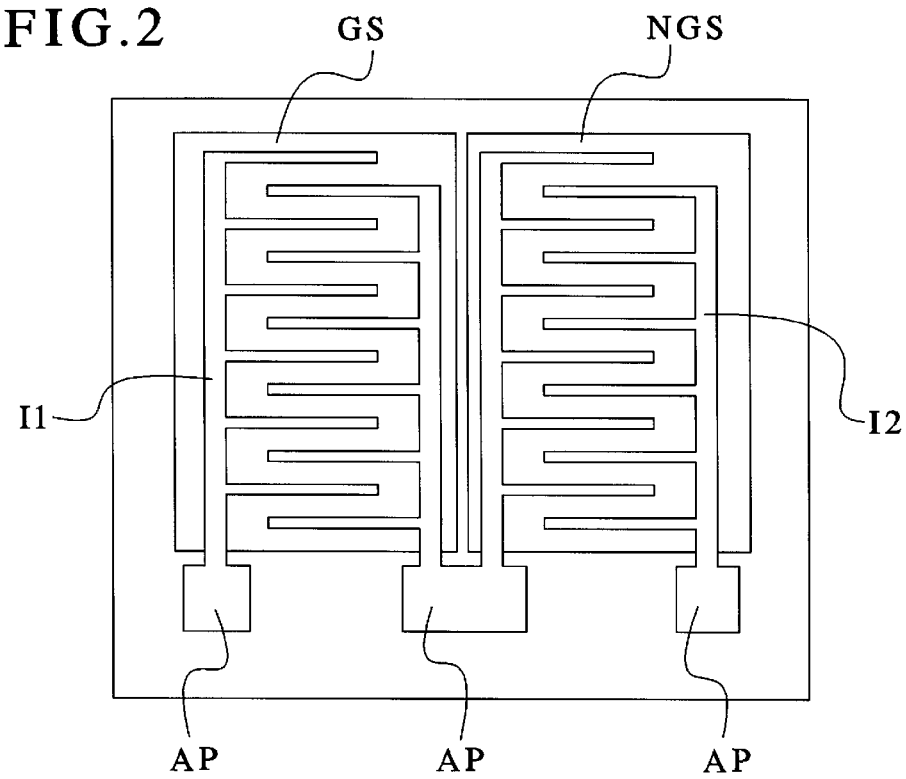
FIG. 2 is a top plan view of a gas sensor made in accordance with the present invention.

Since, as shown in FIG. 2, the reference resistor is located on the same substrate S as the gas-sensitive part GS, and directly next to it, both undergo the same temperature fluctuations. With the same temperature dependence, provided by virtue of the layout of the reference part (non-gas-sensitive part), the gas-sensitive sensor part and the reference part change their electrical resistance equally in the event of temperature fluctuations. The ratio or the difference between the sensor resistance and the reference resistance is not affected by a temperature fluctuation. The temperature therefore needs only to be kept in the range in which the desired gas effect occurs. This means, if the gas sensor is intended to be used for the detection of reducing gases, that the operating temperature should be kept between 600° and 850° C. However, if the gas sensor is intended to be used for the detection of oxygen, the operating temperature should be set at about 950° C.

The two central contacts (contact pads) AP of the interdigital electrode structures I1, I2 are advantageously connected to each other. This is, however, not strictly necessary.

The gas sensor according to the invention has the following advantages:

a) The requirement for temperature control is reduced compared to the prior art mentioned at the start. The temperature fluctuations may extend over the entire temperature range in which the desired gas effect occurs to an appropriate extent.

b) A resistance drift of the gas-sensitive part, because of deterioration, no longer affects the sensor signal since the reference resistor is subject to the same deterioration effects.

c) The use of a resistance ratio or a resistance difference circumvents the problem of having to evaluate high sensor resistances. The requirements made of the evaluation electronics are thereby alleviated.

d) Fluctuations and inaccuracies in the production process for the gas sensor have less effect on the sensor signal in the method which is described. The non-gas-sensitive part NGS, the reference resistor, is applied to the same substrate S as the gas-sensitive part, the gas sensor proper. As far as the deposition of the gas-sensitive or non-gas-sensitive arrangement (sputtering), both undergo the same processes, and therefore substantially the same technical fluctuations.

e) Interactions of the gas-sensitive arrangement with the substrate S do not have such a great effect on the sensor signal. Because of interdiffusion, substrates which have been used to date, for example BeO or $Al_2O_3$ lead to a more or less pronounced resistance increase at high operating temperatures.

The improved properties of the gas sensor can be explained further with the aid of the graphs in FIGS. 3 to 7.

Figure 3:
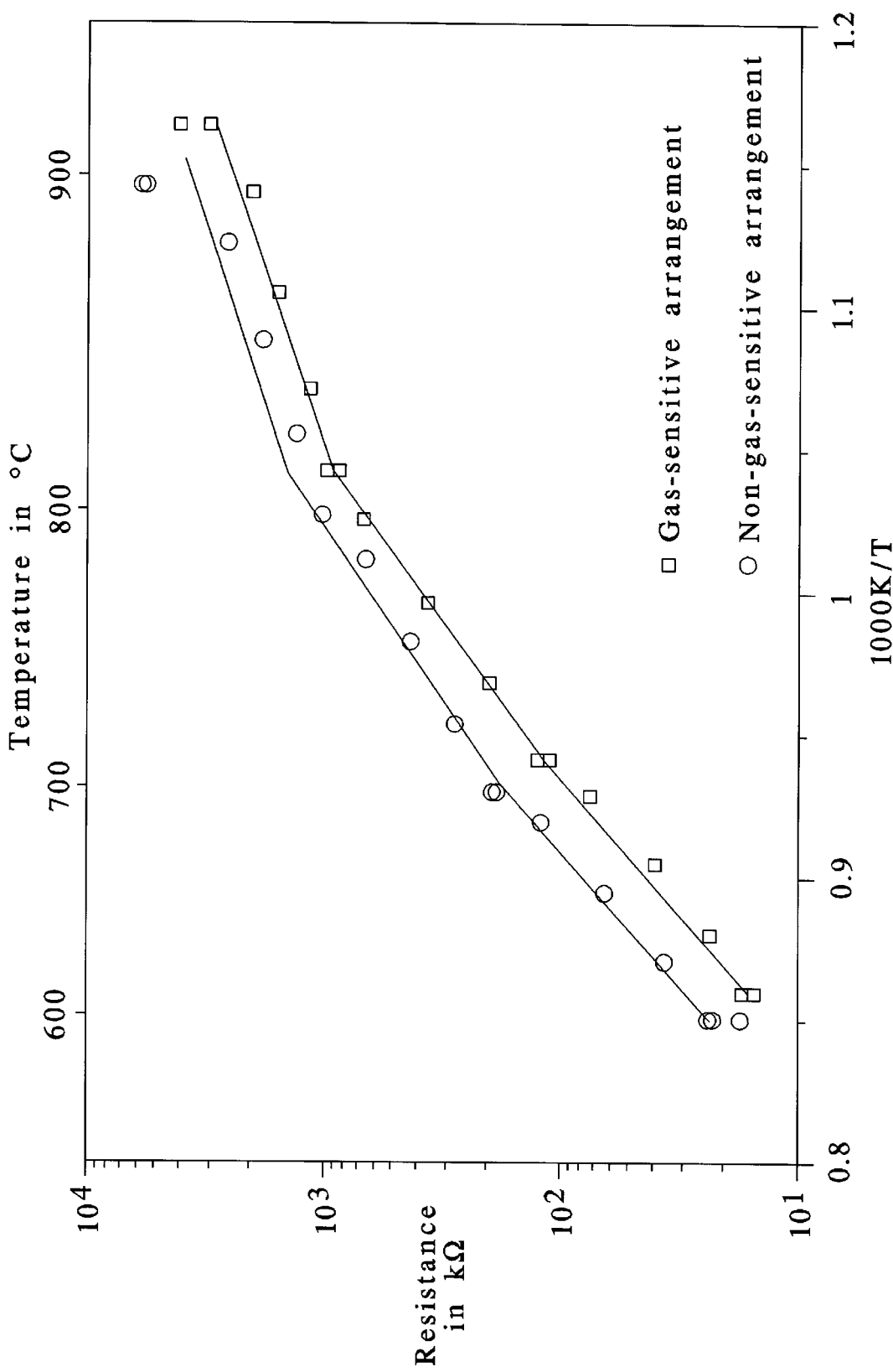
FIG. 3 illustrates, graphically, the resistance as a function of temperature for the gas-sensitive component and the non-gas-sensitive component of the present invention.

From FIG. 3 it is clear that the resistance of the gas-sensitive arrangement GS, compared to that of the non-gas-sensitive arrangement NGS which is used, has the same temperature-dependent change over a wide temperature range.

Figure 4:
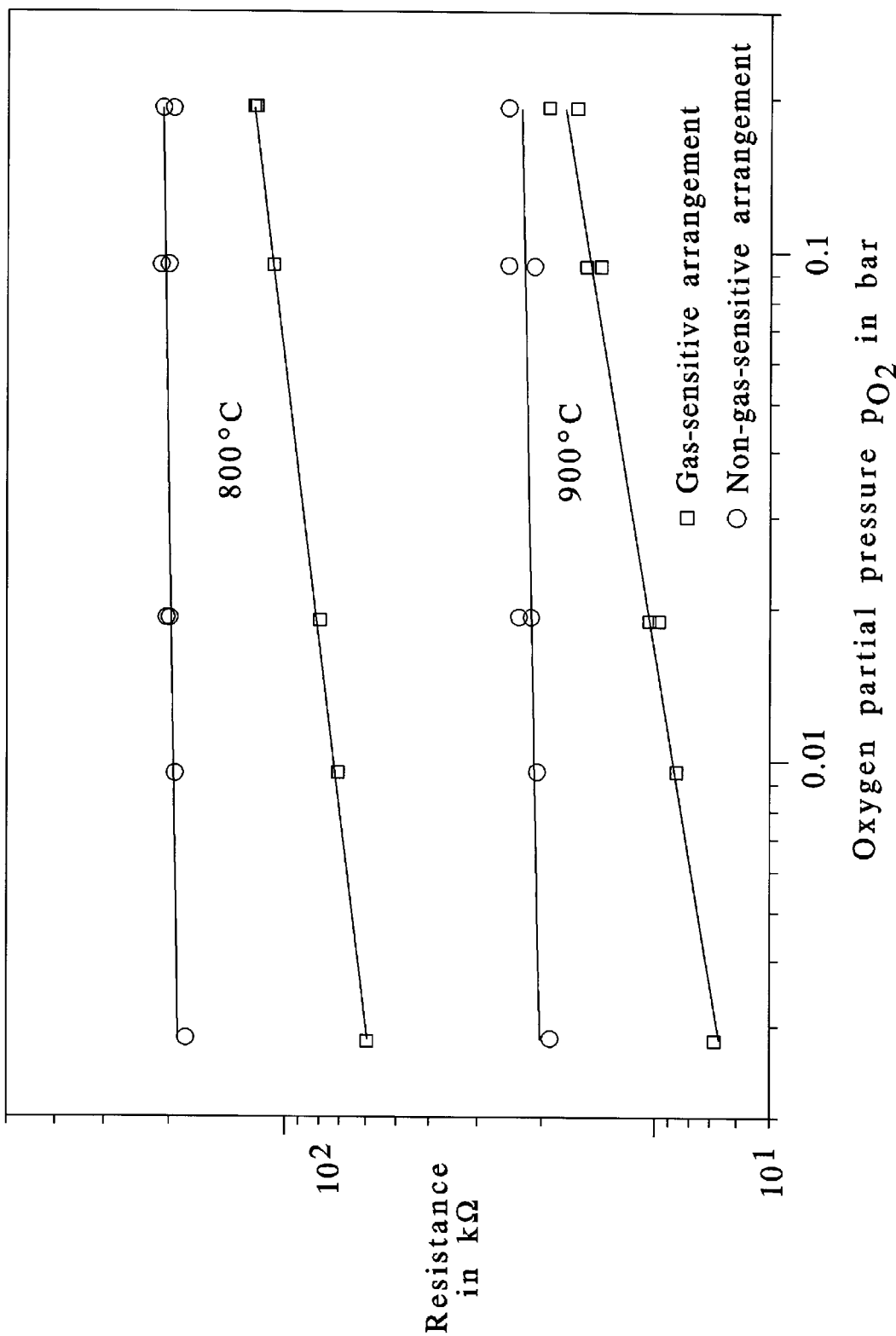
FIG. 4 illustrates, graphically, the dependence of the electrical resistance on the oxygen partial pressure for both the gas-sensitive component and the non-gas-sensitive component of the present invention.

It can be clearly seen from FIG. 4 that the resistance of the non-gas-sensitive arrangement NGS which is used does not significantly change when the partial pressure of the oxygen to be detected changes. In contrast, the resistance of the gas-sensitive arrangement GS does, as desired, have a dependence on the oxygen partial pressure.

Figure 5:
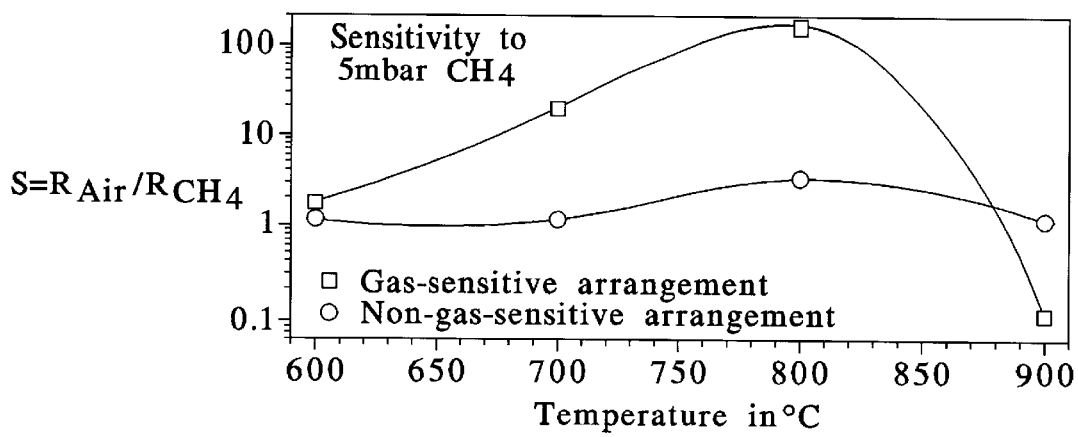
FIG. 5 illustrates, graphically, the different sensitivities of the gas-sensitive component and the non-gas-sensitive component as a function of temperature for $CH_4$.
Figure 6:
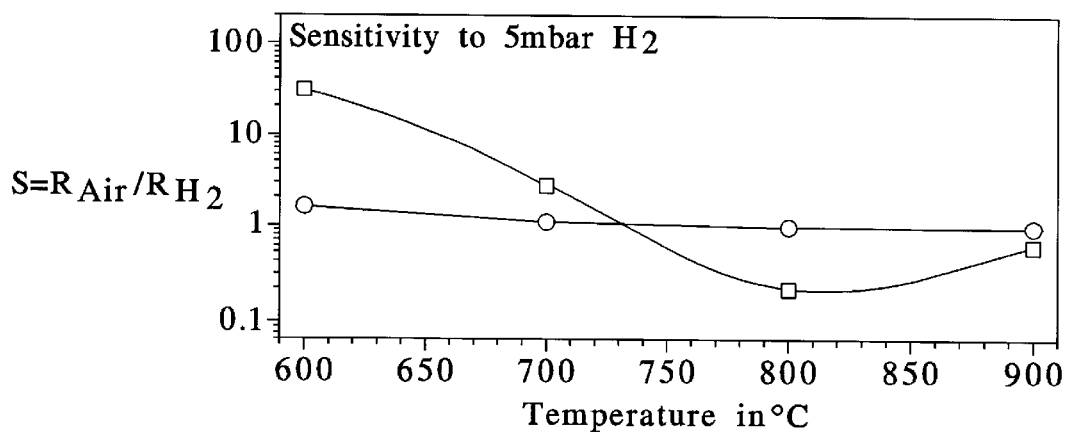
FIG. 6 illustrates, graphically, the different sensitivities of the gas-sensitive component and the non-gas-sensitive component as a function of temperature for $H_2$.
Figure 7:
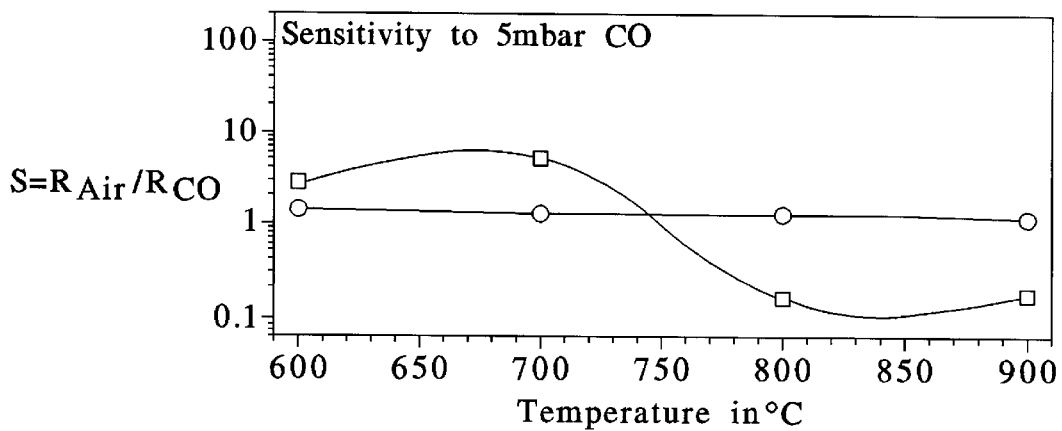
FIG. 7 illustrates, graphically, the different sensitivities of the gas-sensitive component and the non-gas-sensitive component as a function of temperature for CO.

The sensitivity for various reducing gases as a function of the operating temperature, both for the gas-sensitive arrangement GS and for the non-gas-sensitive arrangement NGS are plotted in FIGS. 5, 6 and 7. The best results, for the temperature fluctuations which are recorded from 600° to 900° C., are found for $H_2$ and CO.

Figure 8:
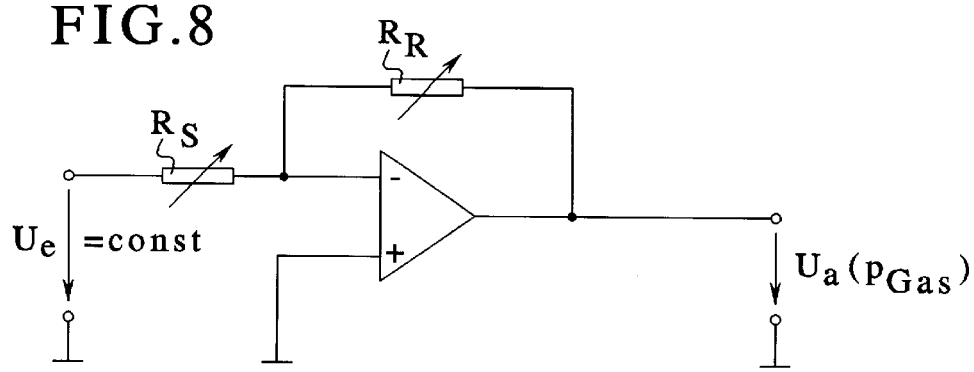
FIG. 8 illustrates, schematically, one embodiment of the evaluation electronics of the present invention.

FIG. 8 represents one possibility of the evaluation electronics for the output signals delivered by the gas sensor. In this case the resistance ratio of the reference part NGS to the gas-sensitive part GS is measured. The sensitivity A is given as:

$$A = \frac{U_a}{U_e} = -\frac{R_R(T)}{R_S(T, p_{Gas})}$$

Figure 9:
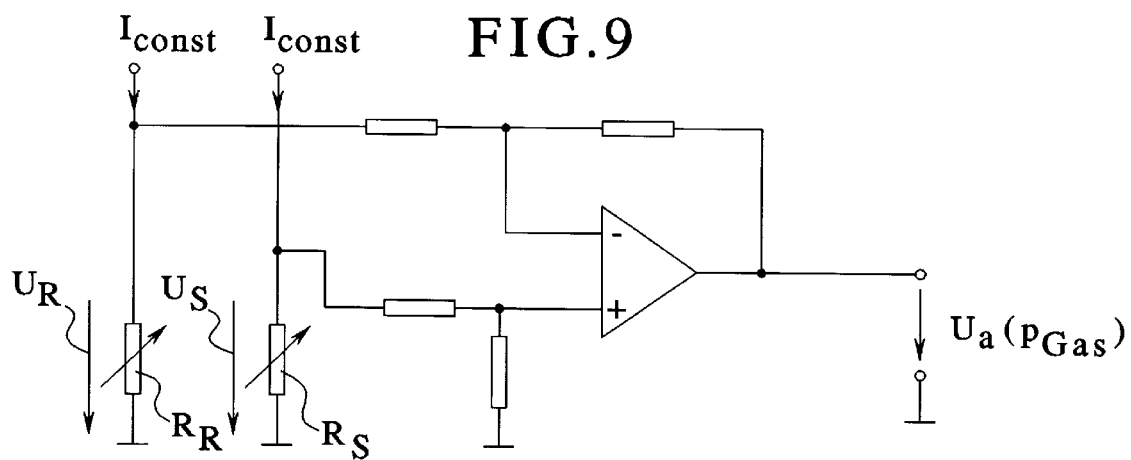
FIG. 9 illustrates, schematically, another embodiment of the evaluation electronics of the present invention.

$U_a$=output voltage
$U_e$=input voltage (=constant)
$R_R(T)$=temperature-dependent resistance of the reference part NGS $R_S(T, P_{Gas})$=temperature-dependent and gas-dependent resistance of the gas-sensitive part GS FIG. 9 shows a further variant of the evaluation electronics. The measurable resistance difference between the reference part NGS and the gas-sensitive part GS is given as:

$$U_a = U_R - U_S$$

$$U_a = I_{const}[R_R(T) - R_S(T, p_{Gas})]$$

$$U_a = I_{const}[R_{RO} - R_{SO} \Delta R_{Gas}]$$

The resistances $R_{RO}$ and $R_{SO}$ are constant values. However, the resistance $\Delta R_{Gas}$ is dependent on the gas.

Figure 10:
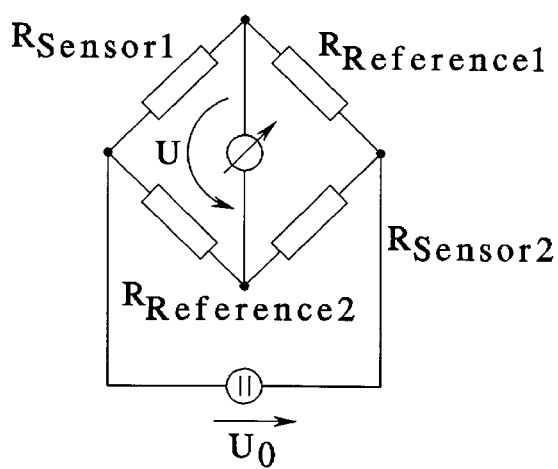
FIG. 10 illustrates, schematically, yet another embodiment of the evaluation electronics of the present invention.

For the third embodiment of the evaluation electronics, shown in FIG. 10, in which two gas sensors are connected together to form a bridge, the measured voltage U is given as:

$$U = \frac{R_S(T, p_{gas}) - R_R(T)}{R_S(T, p_{Gas})} \cdot U_0$$

with:

$$R_s(T, p_{Gas}) = R_{sensor1}(T, p_{Gas}) = R_{sensor2}(T, p_{Gas})$$

$$R_R(T) = R_{Reference1}(T) = R_{Reference2}(T)$$

$U_0$=operating voltage

Figure 11:
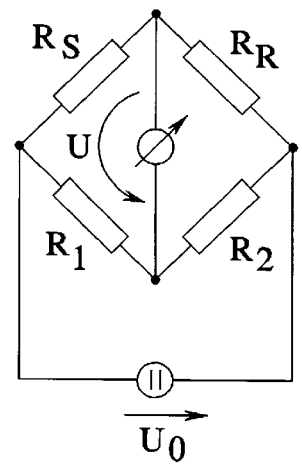
FIG. 11 illustrates, schematically, still another embodiment of the evaluation electronics of the present invention.

For the fourth embodiment of the evaluation electronics, shown in FIG. 11, in which one gas sensor and two fixed-value resistors $R_1$ and $R_2$ are connected together to form a bridge, the measured voltage U is given as:

$$U = \left( \frac{R_S(T, p_{gas})}{R_S(T, p_{Gas}) - R_R(T)} - \frac{R_1}{R_1 + R_2} \right) \cdot U_0$$

The layers are applied to two neighboring interdigital electrode structures I1, I2.

A subsequent heat-treatment at 900° to 1050° C. produces defined conditions for later measurements at 900° C. The heat-treatment does not lead to diffusion out of the intermediate layers.

At temperatures of 600° to 850° C., the gas sensor is suitable for the detection of reducing gases. At 950° C., it is used as an oxygen sensor.

Quartz glass, for example, is suitable as the substrate S.

Amongst other things, the gas sensor can be used for methane or carbon monoxide warning instruments, for small-scale cooking or heating units, or for combustion control systems.

We claim:

1. A gas sensor comprising:

a substrate carrying a first electrode and a second electrode, the first and second electrodes being disposed adjacent to one another, the first electrode being disposed between the substrate and a gas-sensitive component, the gas sensitive component comprising an n-type semiconductor, the gas-sensitive component having a resistance that is gas-dependent and temperature-dependent, and the second electrode being disposed between the substrate and a non-gas-sensitive component, the non-gas-sensitive component comprising a n-type semiconductor and a p-type semiconductor, the non-gas-sensitive component having a resistance that is temperature-dependent and that is not gas-dependent.

2. The gas sensor of claim 1 wherein the n-type semiconductor of the gas-sensitive component is $Ga_2O_3$.

3. The gas sensor of claim 1 wherein the n-type semiconductor of the non-gas-sensitive component is $Ga_2O_3$.

4. The gas sensor of claim 1 wherein the n-type semiconductor of the non-gas-sensitive component is $Ga_2O_3$ and the p-type semiconductor of the non-gas-sensitive component is $ZrO_2$.

5. The gas sensor of claim 1 wherein the n-type semiconductor of the non-gas-sensitive component further comprises at least one layer of a n-type semiconductor material and the p-type semiconductor of the non-gas-sensitive component further comprises at least one layer of a p-type semiconductor material.

6. The gas sensor of claim 5 wherein the n-type and p-type semiconductor layers are heat-treated at temperatures ranging from about 900° C. to about 1050° C.

7. The gas sensor of claim 1 wherein the first electrode comprises an interdigital component.

8. The gas sensor of claim 1 wherein the second electrode comprises an interdigital component.

9. The gas sensor of claim 1 wherein the gas sensor characterized as being able to detect detects reducing gases at temperatures ranging from about 600° C. to about 850° C.

10. The gas sensor of claim 1 wherein the gas sensor detects oxygen at a temperature of about 950° C.

* * * * *